(12) United States Patent
Buettelmann et al.

(10) Patent No.: US 7,241,760 B2
(45) Date of Patent: Jul. 10, 2007

(54) HETEROARYL-SUBSTITUTED IMIDAZOLE DERIVATIVES

(75) Inventors: Bernd Buettelmann, Schopfheim (DE); Simona Maria Ceccarelli, Basel (CH); Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 397 days.

(21) Appl. No.: 10/866,255

(22) Filed: Jun. 12, 2004

(65) Prior Publication Data
US 2004/0254179 A1    Dec. 16, 2004

(30) Foreign Application Priority Data
Jun. 12, 2003   (EP) .................................. 03012290

(51) Int. Cl.
- A61K 31/5377 (2006.01)
- A61K 31/50 (2006.01)
- C07D 401/04 (2006.01)
- C07D 403/04 (2006.01)
- C07D 413/04 (2006.01)

(52) U.S. Cl. .................... 514/235.8; 544/111; 544/139; 544/224; 544/238; 546/184; 546/192; 546/207; 546/210; 514/231.2; 514/231.5; 514/247; 514/252.05

(58) Field of Classification Search ................. 544/224, 544/238, 111, 139; 514/247, 252.01, 252.05, 514/231.2, 231.5, 231.6; 546/184, 192, 207, 546/210
See application file for complete search history.

(56) References Cited

U.S. PATENT DOCUMENTS 5,354,867 A *   10/1994   Carini et al. ................. 548/252
6,706,707 B2 *   3/2004   Mutel et al. ................. 514/224.8
6,927,232 B2 *   8/2005   Mutel et al. ................. 514/399

FOREIGN PATENT DOCUMENTS

| WO | WO 99/02497 A2 | 1/1999 |
|---|---|---|
| WO | WO 01/16121 A1 | 3/2001 |
| WO | WO 02/08205 A1 | 1/2002 |
| WO | WO 02/46166 A1 | 6/2002 |

OTHER PUBLICATIONS

Fabrizio Gasparini et al, Neuropharmacology Pergamon Press, XP001032948, vol. 38, No. 10, pp. 1493-1503 (1999).
Will P.J.M. Spooren et al, Trends in Pharmacological Sciences, Elsevier Trends Journal, XP004247865, vol. 22, No. 7, pp. 331-337 (2001).
Buchwald et al., An Efficient Copper-Catalyzed Coupling of Aryl Halides with Imidazoles, Tetrahedron Letters, 1999, pp. 2657-2660, 40.
Cliff et al., Synthesis of 4,4'-Biimidazoles, Synthesis, Jul. 1994, pp. 681-682.
Collman et al., An Efficient Diamine Copper Complex-Catalyzed Coupling of Arylboronic Acids with Imidazoles.
Ohira, Susumu, Methanolysis of Dimethyl (1-Diazo-2-Oxopropyl)Phosphonate and Reaction with Carbonyl Compounds, Synthetic Communications, 1989, pp. 561-564, 19(3&4).
Sonogashira et al., A Convenient Synthesis of 1-Alkynyl Ketones and 2-Alkynamides, Synthesis, Nov. 1977, pp. 777-778.

* cited by examiner

*Primary Examiner*—Golam M. M. Shameem
(74) *Attorney, Agent, or Firm*—George W. Johnston; Patricia S. Rocha-Tramaloni; Gene J. Yao

(57) ABSTRACT

The present invention relates to imidazole derivatives of the general formula

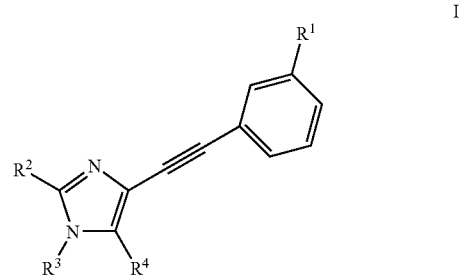

wherein $R^1$, $R^2$, $R^3$ and $R^4$ are described hereinbelow. These compounds can be used in the treatment or prevention of mGluR5 receptor mediated disorders. These compounds are useful, interalia, in the treatment or prevention of acute and/or chronic neurological disorders such as psychosis, epilepsy, schizophrenia, Alzheimer's disease, cognitive disorders and memory deficits, as well as chronic and acute pain.

15 Claims, No Drawings

HETEROARYL-SUBSTITUTED IMIDAZOLE DERIVATIVES

FIELD OF THE INVENTION

The present invention relates to imidazole derivatives of formula I

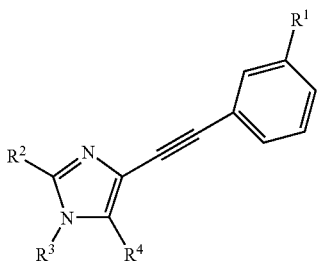

wherein $R^1$, $R^2$, $R^3$ and $R^4$ are described hereinbelow. These compounds can be used in the treatment or prevention of mGluR5 receptor mediated disorders. These compounds are useful, interalia, in the treatment or prevention of acute and/or chronic neurological disorders such as psychosis, epilepsy, schizophrenia, Alzheimer's disease, cognitive disorders and memory deficits, as well as chronic and acute pain.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I; mGluR2 and mGluR3 belong to group II; and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)). Selective mGluR5 antagonists are especially useful for the treatment of anxiety and pain.

SUMMARY OF THE INVENTION

The invention relates to a compound of formula I

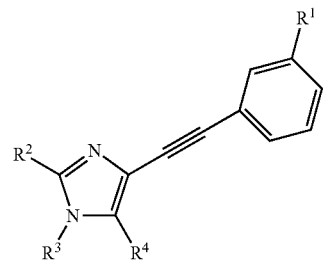

wherein $R^1$ is selected from the group consisting of halogen, lower alkyl, lower alkoxy, $CF_3$, $CF_2H$, $OCF_3$, $OCF_2H$ and cyano;

$R^2$ is lower alkyl;

$R^3$ is selected from
 heteroaryl,
 heteroaryl substituted by one, two or three substituents, selected from the group consisting of
  halogen,
  lower alkyl,
  cycloalkyl,
  lower alkyl-halogen,
  cyano,
  lower alkoxy,
  NR'R",
  1-morpholinyl,
  1-pyrrolidinyl,
  1-pyrrolidinyl substituted by —OR or $CH_2OR$,
  piperidinyl,
  piperidinyl substituted by —OR or $CH_2OR$,
  thiomorpholinyl,
  1-oxo-thiomorpholinyl,
  1,1-dioxo-thiomorpholinyl,
  piperazinyl, and
  piperazinyl substituted by a substituent selected from lower
  alkyl, cycloalkyl and $CH_2$-cycloalkyl;

R is selected from the group consisting of hydrogen, lower alkyl, cycloalkyl and $CH_2$-cycloalkyl;

R' and R" are each independently selected from the group consisting of hydrogen, lower alkyl, cycloalkyl, $CH_2$-cycloalkyl, —OR and $CH_2$—OR;

$R^4$ is selected from hydrogen, C(O)H, and $CH_2R^5$; and
$R^5$ is selected from the group consisting of hydrogen, OH, $C_1$–$C_6$-alkyl, and $C_3$–$C_{12}$-cycloalkyl;

or a pharmaceutically acceptable salt thereof.

Another embodiment of this invention is related to a process for preparing a compound according to general formula I following the general procedures as outlined above for compounds of formula I. Yet another embodiment is related to a pharmaceutical composition containing one or more compounds of the present invention and pharmaceutically acceptable excipients for the treatment and prevention of mGluR5 receptor mediated disorders, such as acute and/or chronic neurological disorders, in particular anxiety and chronic or acute pain. Yet another embodiment of this invention is related to a method of treatment and prevention of mGluR5 receptor mediated disorders as outlined above.

DETAILED DESCRIPTION OF THE INVENTION

The following definitions of general terms used in the present description apply irrespective of whether the terms in question appear alone or in combination. The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "lower alkoxy" denotes a group wherein the alkyl residues are as defined above and which is attached via an oxygen atom.

The term "halogen" denotes fluorine, chlorine, bromine and iodine.

The term "heteroaryl" refers to an aromatic 5- or 6-membered ring containing one or more heteroatoms selected from nitrogen, oxygen or sulphur. Preferred are those heteroaryl groups selected from nitrogen or oxygen. Especially preferred are the groups pyrazinyl, pyridinyl, pyrimidinyl, pyridazinyl or furanyl. Examples of such especially preferred heteroaryl groups are pyridin-2,3 or 4-yl, pyrimidin-2-yl, pyridazin-3 or 5-yl or furan-3-yl.

The term "cycloalkyl" denotes a saturated carbocyclic group, containing 3–12 carbon atoms, preferably, 3–6 carbon atoms.

The term "pharmaceutically acceptable salt" refers to any salt derived from an inorganic or organic acid or base.

One embodiment of the present invention is related to a compound of formula I

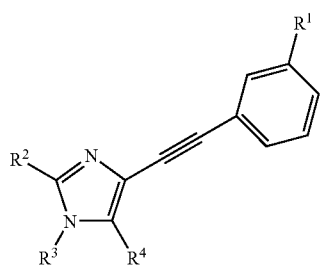

wherein
$R^1$ is selected from the group consisting of halogen, lower alkyl, lower alkoxy, $CF_3$, $CF_2H$, $OCF_3$, $OCF_2H$, and cyano;
$R^2$ is lower alkyl;
$R^3$ is selected from
  heteroaryl, and
  heteroaryl substituted by one, two or three substituents, selected from the group consisting of
    halogen,
    lower alkyl,
    cycloalkyl,
    lower alkyl-halogen,
    cyano,
    lower alkoxy,
    NR'R",
    1-morpholinyl,
    1-pyrrolidinyl,
    1-pyrrolidinyl substituted by —OR or $CH_2OR$,
    piperidinyl,
    piperidinyl substituted by —OR or $CH_2OR$,
    thiomorpholinyl,
    1-oxo-thiomorpholinyl,
    1,1-dioxo-thiomorpholinyl,
    piperazinyl, and
    piperazinyl substituted by a substituent selected from lower
      alkyl, cycloalkyl and $CH_2$-cycloalkyl;
R is selected from the group consisting of hydrogen, lower alkyl, cycloalkyl and $CH_2$-cycloalkyl;
R' and R" are each independently selected from the group consisting of hydrogen, lower alkyl, cycloalkyl, $CH_2$-cycloalkyl, —OR and $CH_2$—OR;
$R^4$ is selected from hydrogen, C(O)H, and $CH_2R^5$; and
$R^5$ is selected from the group consisting of hydrogen, OH, $C_1$–$C_6$-alkyl, and $C_3$–$C_{12}$-cycloalkyl;

or a pharmaceutically acceptable salt thereof.

Another embodiment of the present invention is related to a compound of formula I

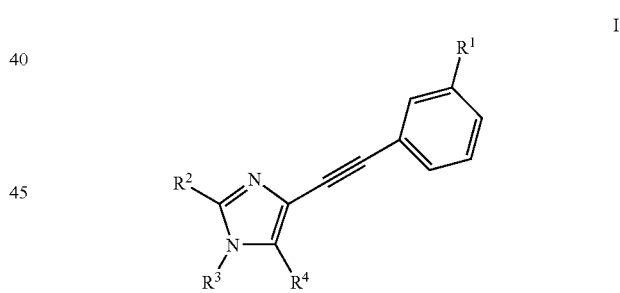

wherein
$R^1$ is selected from halogen and cyano;
$R^2$ is lower alkyl;
$R^3$ is selected from
  heteroaryl, and
  heteroaryl substituted by one or two substituents, selected from the group consisting of
    halogen,
    lower alkyl,
    lower alkyl-halogen,
    lower alkoxy,
    NR'R",
    thiomorpholinyl, and
    1,1-dioxo-thiomorpholinyl;
R is selected from the group consisting of hydrogen, lower alkyl, cycloalkyl and $CH_2$-cycloalkyl;

R' and R" are each lower alkyl; and
R⁴ is hydrogen;
or a pharmaceutically acceptable salt thereof.

Encompassed in formula I is also a compound of formula IA:

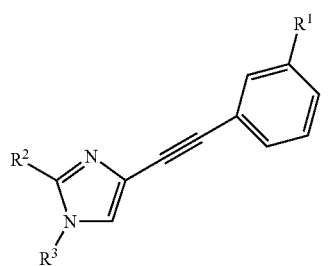

IA wherein
R¹ is selected from the group consisting of halogen, lower alkyl, lower alkoxy, CF₃ and cyano;
R² is lower alkyl;
R³ is selected from
  heteroaryl, and
  heteroaryl substituted by one, two or three substituents, selected from the group consisting of
    halogen,
    lower alkyl,
    lower alkyl-halogen,
    cyano,
    NR'R",
    1-morpholinyl,
    1-pyrrolidinyl,
    1-pyrrolidinyl substituted by —OR or CH₂OR,
    piperidinyl,
    piperidinyl substituted by —OR or CH₂OR,
    1,1-dioxo-thiomorpholinyl,
    piperazinyl,
    piperazinyl substituted by a substituent selected from lower alkyl or (CH₂)₀,₁-cycloalkyl;
R is selected from the group consisting of hydrogen, lower alkyl and CH₂-cycloalkyl; and
R' and R" are independently selected from the group consisting of hydrogen, lower alkyl, cycloalkyl, CH₂-cycloalkyl, OR and CH₂OR;

or a pharmaceutically acceptable salt thereof.

One embodiment of the compound of formula I in the present invention is where R¹ is halogen and R³ is heteroaryl.

Another embodiment of the compound of formula I in the present invention is where R¹ is halogen and R³ is heteroaryl substituted by one or two lower alkyl-halogen.

Another embodiment of the compound of formula I in the present invention is where R¹ is cyano and R³ is heteroaryl substituted by one or two lower alkyl.

Another embodiment of the compound of formula I in the present invention is where R¹ is cyano and R³ is selected from heteroaryl substituted by one or two lower alkyl-halogen.

Another embodiment of the compound of formula I in the present invention is where R¹ is cyano and R³ is lower alkyl.

Another embodiment of the compound of formula I in the present invention is where R¹ is halogen and R³ is heteroaryl substituted by one or two halogen.

Another embodiment of the compound of formula I in the present invention is where R¹ is halogen and R³ is heteroaryl substituted by one or two lower alkyl.

Another embodiment of the compound of formula I in the present invention is where R¹ is cyano and R³ is heteroaryl substituted by one or two lower alkoxy.

Another embodiment of the compound of formula I in the present invention is where R¹ is halogen and R³ is heteroaryl substituted by one or two lower alkoxy.

Another embodiment of the compound of formula I in the present invention is where R¹ is halogen and R³ is heteroaryl substituted by one or two NR'R", where R' and R" are each lower alkyl.

Another embodiment of the compound of formula I in the present invention is where R¹ is CF₃ and R³ is heteroaryl substituted by one or two lower alkyl.

Another embodiment of the compound of formula I in the present invention is where R¹ is CF₃ and R³ is heteroaryl substituted by one or two halogen.

Another embodiment of the compound of formula I in the present invention is where R¹ is cyano and R³ is heteroaryl substituted by NR'R", where R' and R" are each lower alkyl.

Another embodiment of the compound of formula I in the present invention is where R¹ is halogen and R³ is heteroaryl substituted by thiomorpholinyl.

Another embodiment of the compound of formula I in the present invention is where R¹ is halogen and R³ is heteroaryl substituted by 1,1-dioxo-thiomorpholinyl.

Preferred compounds of formula I are those, in which R¹ is chloro or cyano.

Especially preferred are those compounds from this group, in which R³ is unsubstituted or substituted pyrimidin-2yl, for example the following compounds:
2-[4-(3-chloro-phenylethynyl)-2-methyl-imidazol-1-yl]-pyrimidine,
2-[4-(3-chloro-phenylethynyl)-2-methyl-imidazol-1-yl]-4-trifluoromethyl-pyrimidine,
2-[4-(3-chloro-phenylethynyl)-2-methyl-imidazol-1-yl]-4-methyl-pyrimidine,
2-[4-(3-chloro-phenylethynyl)-2-methyl-imidazol-1-yl]-5-fluoro-pyrimidine and
3-[1-(4-Methoxy-pyrimidin-2-yl)-2-methyl-1H-imidazol-4-ylethynyl]-benzonitrile.

Especially preferred are further those compounds of this group, wherein R³ is unsubstituted or substituted pyridin-2-yl, for example the following compounds:
3-[2-methyl-1-(6-methyl-pyridin-2-yl)-1H-imidazol-4-ylethynyl]-benzonitrile,
3-[2-methyl-1-(6-trifluoromethyl-pyridin-2-yl)-1H-imidazol-4-ylethynyl]-benzonitrile,
3-[2-methyl-1-(5-methyl-pyridin-2-yl)-1H-imidazol-4-ylethynyl]-benzonitrile,
3-[2-methyl-1-(4-methyl-pyridin-2-yl)-1H-imidazol-4-ylethynyl]-benzonitrile,
2-[4-(3-chloro-phenylethynyl)-2-methyl-imidazol-1-yl]-6-methyl-pyridine,
2-[4-(3-chloro-phenylethynyl)-2-methyl-imidazol-1-yl]-6-trifluoromethyl-pyridine,
2-[4-(3-chloro-phenylethynyl)-2-methyl-imidazol-1-yl]-5-methyl-pyridine,
3-[4-(3-chloro-phenylethynyl)-2-methyl-imidazol-1-yl]-5-fluoro-pyridine,
2-[4-(3-chloro-phenylethynyl)-2-methyl-imidazol-1-yl]-5-methyl-pyridine,
2-[4-(3-chloro-phenylethynyl)-2-methyl-imidazol-1-yl]-4-methyl-pyridine, 3-[4-(3-chloro-phenylethynyl)-2-methyl-imidazol-1-yl]-5-fluoro-pyridine and
4-{6-[4-(3-chloro-phenylethynyl)-2-methyl-imidazol-1-yl]-pyridin-2-yl}-thiomorpholine.

Further preferred are those compounds of this group, wherein $R^3$ is unsubstituted or substituted pyridin-3-yl, for example the following compounds:
2-chloro-5-[4-(3-chloro-phenylethynyl)-2-methyl-imidazol-1-yl]-pyridine or
2-[4-(3-chloro-phenylethynyl)-2-methyl-imidazol-1-yl]-4-methyl-pyridine.

Preferred are further those compounds of this group, wherein $R^3$ is pyridazinyl or pyrazinyl which may be substituted or unsubstituted, for example the following compounds:
5-[4-(3-chloro-phenylethynyl)-2-methyl-imidazol-1-yl]-3-methyl-pyridazine,
3-[4-(3-chloro-phenylethynyl)-2-methyl-imidazol-1-yl]-6-methyl-pyridazine and
2-[4-(3-Chloro-phenylethynyl)-2-methyl-imidazol-1-yl]-pyrazine Further preferred are those compounds of this group, wherein $R^3$ is furan-3-yl, for example the following compound:
5-(3-chloro-phenylethynyl)-1-furan-3-yl-2-methyl-1H-imidazole.

The compounds of formula I or IA of the invention may be prepared according to a process which comprises reacting a compound of formula II

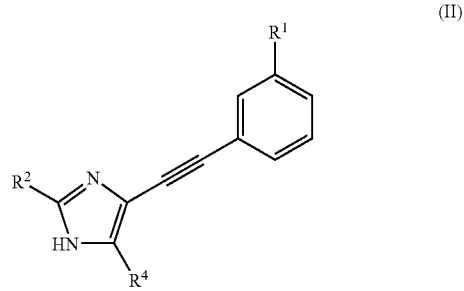

wherein $R^1$, $R^2$ and $R^4$ have the meanings as defined above, with a compound of formula III $$R^3\text{-}Z \quad \text{(III)}$$

wherein $R^3$ has the meanings as defined above and Z is halogen or $B(OH)_2$.

The reaction as described above may be carried out in accordance with standard procedures, e.g. by arylation of a compound of formula II using an aromatic boronic acid and a copper catalyst in a solvent like dichloromethane or tetrahydrofurane [see e.g. Colmann et al., Org. Lett. 2:1233 (2000)] or by heating a compound of formula II and a compound of formula III wherein Z is halogen with a base like potassium carbonate or cesium carbonate in a solvent like dimethylformamide, or Pd catalyzed according to Buchwald conditions [see e.g. Example 8; Buchwald et al., Tetrahedron Lett. 40:2657 (1999)].

In another embodiment, the compounds of formula I or IA of the invention may be prepared according to a process which comprises reacting a compound of formula IV

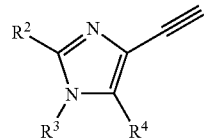

wherein $R^2$, $R^3$ and $R^4$ have the meanings as defined above, with a compound of formula V

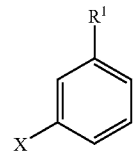

wherein $R^1$ has the meanings as defined above and X is halogen.

The reaction described above may be carried out by a Sonogashira coupling of a compound of formula IV and a compound of formula V in the presence of, e.g., CuI, $(Ph_3P)_2PdCl_2$, $Et_3N$ in a solvent like tetrahydrofuran or dimethylformamide [Sonogashira et al., Synthesis 777 (1977)]. In one embodiment the meaning X in compounds of formula V is bromine or iodine.

In yet another embodiment, the compounds of formula I or IA of the invention may be prepared according to a process which comprises reacting a compound of formula VI

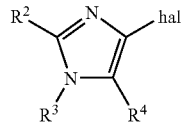

wherein $R^2$, $R^3$ and $R^4$ have the meanings as defined above and hal is halogen, with a compound of formula VII

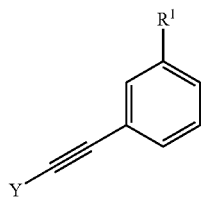

wherein $R^1$ has the meaning as defined above and Y is trimethylsilyl or hydrogen.

The reaction described above may, e.g. be carried out in the presence of CuI, $(Ph_3P)_2PdCl_2$, $Et_3N$, $n\text{-}Bu_4F$ in a solvent like tetrahydrofuran or dimethylformamide.

If desired, the above compounds obtained may be converted into their pharmaceutically acceptable salts.

The salt forms are made by standard procedures known to the skilled artisan.

The compounds of formulae II, IV, VI und VII are novel and also an embodiment of the present invention.

The compounds of formulae III and V are commercially available or their preparation is known to the skilled artisan.

The compounds of formula II may be prepared by reacting a compound of formula VIII

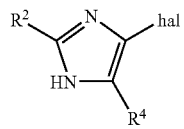

(VIII)

wherein $R^2$ and $R^4$ have the above meanings and hal is halogen, with a compound of formula VII as above.

The compounds of formula VIII may be prepared as described e.g. in Cliff and Pyne [Synthesis 681–682 (1994)].

The compounds of formula IV may be prepared by reacting a compound of formula IX

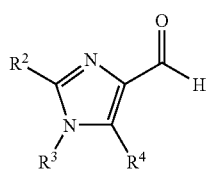

(IX)

wherein $R^2$, $R^3$ and $R^4$ have the meanings as defined above, with dimethyl (1-diazo-2-oxopropyl)phosphonate as described in Ohira [Synth.Comm. 19:561–564 (1989)].

Compounds of formula VI may be prepared by reacting a compound of formula VIII as above with a compound of formula X

R³—B(OH)₂ (X)

wherein $R^3$ has the meanings as defined above.

The reaction may take place by arylation of a compound of formula VIII using an aromatic boronic acid (compound of formula X) and a copper catalyst in a solvent like dichloromethane or tetrahydrofurane under an oxygen atmosphere [see e.g. Colmann et al., Org.Lett. 2:1233 (2000)].

Compounds of formula VII may be prepared by reacting a compound of formula V as above with a compound of formula XI

(XI)

The reaction may take place by a Sonogashira coupling in the presence of eg. CuI, (Ph₃P)₂PdCl₂, Et₃N in a solvent like tetrahydrofuran or dimethylformamide [Sonogashira et al., Synthesis 777 (1977)].

Compounds of formula IX may be prepared by oxidizing a compound of formula XII

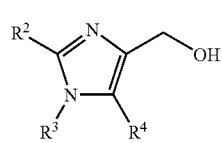

(XII)

according to methods known to the skilled artisan.

Compounds of formula XII may be prepared by deprotecting a compound of formula XIII

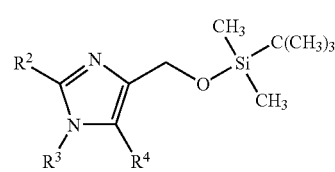

(XIII)

according to methods known to the skilled artisan.

Compounds of formula XIII may be prepared by alkylating a compound of formula XIV

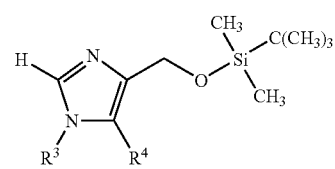

(XIV)

with an alkylating agent of formula XVa

R²-hal (XVa)

according to methods known to the skilled artisan.

Starting compounds of formula XVa are commercially available.

Compounds of formula XIV may be prepared by treating a compound of formula XV

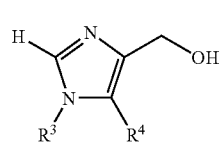

(XV)

with tert.-butyl dimethyl silyl chloride according to methods known to the skilled artisan.

Compounds of formula XV may be prepared by treating a compound of formula XVI

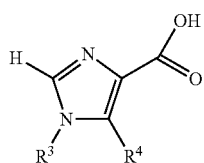

(XVI)

with a reducing agent according to methods known to the skilled artisan.

Compounds of formula XVI may be prepared by hydrolysing a compound of formula XVII

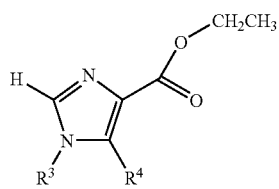

(XVII)

according to methods known to the skilled artisan.

Compounds of formula XVII may be prepared by treating a compound of formula XVIII $R^3$—$NH_2$ (XVIII)

with e.g. triethyl orthoformate, ethylnitro acetate, glacial acetic acid and iron powder according to methods known to the skilled artisan.

Compounds of formula XVIII are commercially available.

The compounds of general formula I, IA and their pharmaceutically acceptable salts can also be manufactured by the general procedure, as shown below:

a) reacting a compound of formula

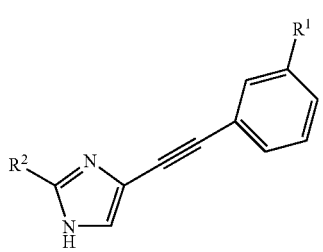

II with a compound of formula $R^3$-Z   III wherein $R^3$ has the meanings as defined above and Z is halogen or $B(OH)_2$, to a compound of formula

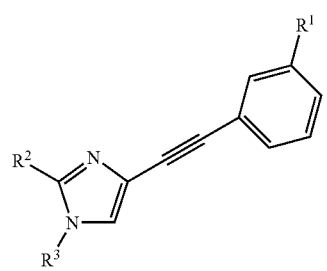

IA wherein $R^1$, $R^2$ and $R^3$ are as described above and Hal is halogen, preferably chloro or fluoro, and if desired, when $R^4$ is other than hydrogen, a) reacting the compound of formula IA with a compound of formula:

$R^4$Hal   VI to a compound of formula

I wherein $R^1$, $R^2$, $R^3$ and $R^4$ are as described above, and if desired, converting the compounds obtained into pharmaceutically acceptable salts.

The procedure is summarized in scheme 1.

The starting materials are known compounds or may be prepared according to methods known in the art, for example as described in example C.

Scheme 1

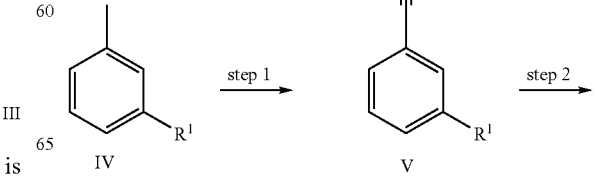

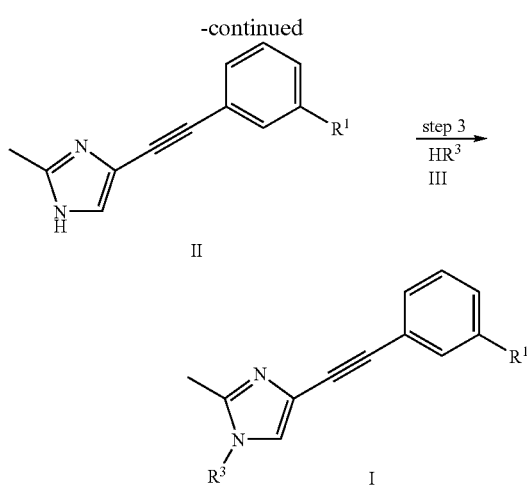

Step 1

A compound of formula IV, for example 1-chloro-3-iodobenzene is dissolved in THF and triethyl amine. This mixture is evacuated and backfilled with argon to remove oxygen from the solution. Triphenylphosphine and bis(triphenylphosphine)palladium(II)chloride are added and the reaction mixture is stirred at room temperature for about 1 h. Copper(I)iodide and trimethylsilylacetylen are added. The reaction mixture is stirred at room temperature overnight. After purification the desired product of formula V is obtained.

Step 2

Solution 1: The obtained compound of formula V, for example (3-chloro-phenylethynyl)-trimethyl-silane and 5-iodo-2-methyl-1H-imidazole (synthesis: M. D. Cliff, S. G. Pyne, *Synthesis* 1994, 681–682) are dissolved in dry THF and dry DMF. This mixture is evacuated and backfilled with argon to remove oxygen from the solution. Solution 2: Triphenylphosphine, bis(triphenylphosphine)-palladium(II) chloride, copper(I)iodide and triethyl amine are dissolved in dry THF. This mixture was also evacuated and backfilled with argon to remove oxygen from the solution.

Solution 2 is heated to about 40° C. and solution 1 is added dropwise. The reaction mixture is heated to about 60° C. and tetrabutylammonium fluoride solution is added dropwise. The reaction is then stirred at room temperature overnight. After purification the desired product of formula II is obtained. This material which still contained tetrabutylammonium salts is used without any further purification for the next step.

Step 3

The compound of formula II, for example 4-(3-chloro-phenylethynyl)-2-methyl-1H-imidazole is dissolved in dimethyl formamide. Potassium carbonate and a compound of formula III, for example 2-chloro-pyrimidine are added and the reaction mixture is stirred at about 80° C. overnight. After work-up and purification the desired compound of formula I is obtained.

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulfonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method:

For binding experiments, cDNA encoding human mGlu 5a receptor was transiently transfected into EBNA cells using a procedure described by Schlaeger and Christensen [Cytotechnology 15:1–13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 µg protein/well.

Saturation isotherms were determined by addition of twelve [$^3$H]MPEP concentrations (0.04–100 nM) to these membranes (in a total volume of 200 µl) for 1 h at 4° C. Competition experiments were performed with a fixed concentration of [$^3$H]MPEP (2 nM) and $IC_{50}$ values of test compounds evaluated using 11 concentrations (0.3–10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 µM MPEP. The radioactivity on the filter was counted (3 min) on a Packard Top-count microplate scintillation counter with quenching correction after addition of 45 µl of microscint 40 (Can berra Packard S. A., Zürich, Switzerland) and shaking for 20 min. For functional assays, [$Ca^{2+}$]i measurements were performed as described previously by Porter et al. [Br. J. Pharmacol. 128:13–20 (1999)] on recombinant human mGlu 5a receptors in HEK-293 cells. The cells were dye loaded using Fluo 4-AM (obtainable by FLUKA, 0.2 µM final concentration). $[Ca^{2+}]i$ measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving $IC_{50}$, and Hill coefficient using an iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

The compounds of the present invention are mGluR 5a receptor antagonists. The activities of compounds of formula I as measured in the assay described above are in the range of $K_i < 160$ nM.

Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

| Example No. | Ki (nM) | Example No. | Ki (nM) | Example No. | Ki (nM) | Example No. | Ki (nM) |
|---|---|---|---|---|---|---|---|
| 1 | 63 | 9 | 11 | 26 | 94 | 35 | 39 |
| 2 | 28 | 20 | 11 | 27 | 130 | 38 | 99 |
| 3 | 31 | 22 | 60 | 31 | 88 | 39 | 9 |
| 8 | 157 | 25 | 32 | 33 | 66 | 40 | 68 |

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary.

The following examples are provided to further elucidate the invention:

EXAMPLE 1

2-[4-(3-Chloro-phenylethynyl)-2-methyl-imidazol-1-yl]-pyrimidine 4-(3-Chloro-phenylethynyl)-2-methyl-1H-imidazole (200 mg, 0.92 mmol) was dissolved in 5 mL dimethyl formamide. Potassium carbonate (255 mg, 1.85 mmol) and 2-chloro-pyrimidine (159 mg, 1.38 mmol) were added and the reaction mixture was stirred at 80° C. overnight. The reaction mixture was poured into 70 mL water and extracted three times with ethyl acetate (100 mL each). The combined organic extracts were dried with sodium sulfate, filtered and evaporated. The crude product was recrystallized from diisopropyl ether and the desired compound was obtained as an off-white solid (212 mg, 78%), MS:m/e=295.1 (M+H$^+$).

EXAMPLE 2

2-[4-(3-Chloro-phenylethynyl)-2-methyl-imidazol-1-yl]-4-trifluoromethyl-pyrimidine The title compound, MS: m/e=363.1 (M+H$^+$), was prepared in accordance with the general method of example 1 from 4-(3-chloro-phenylethynyl)-2-methyl-1H-imidazole and 2-chloro-4-(trifluoromethyl)pyrimidine.

EXAMPLE 3

3-[2-Methyl-1-(6-methyl-pyridin-2-yl)-1H-imidazol-4-ylethynyl]-benzonitrile

The title compound, MS: m/e=299.2 (M+H$^+$), was prepared in accordance with the general method of example 1 from 3-(2-methyl-1H-imidazol-4-ylethynyl)-benzonitrile and 2-fluoro-6-methylpyridine.

EXAMPLE 4

3-[2-Methyl-1-(6-trifluoromethyl-pyridin-2-yl)-1H-imidazol-4-ylethynyl]-benzonitrile The title compound, MS: m/e=353.1 (M+H$^+$), was prepared in accordance with the general method of example 1 from 3-(2-methyl-1H-imidazol-4-ylethynyl)-benzonitrile and 2-fluoro-6-trifluoromethylpyridine.

EXAMPLE 5

3-[2-Methyl-1-(5-methyl-pyridin-2-yl)-1H-imidazol-4-ylethynyl]-benzonitrile

The title compound, MS: m/e=299.2 (M+H$^+$), was prepared in accordance with the general method of example 1 from 3-(2-methyl-1H-imidazol-4-ylethynyl)-benzonitrile and 2-fluoro-5-methylpyridine.

EXAMPLE 6

3-[2-Methyl-1-(4-methyl-pyridin-2-yl)-1H-imidazol-4-ylethynyl]-benzonitrile

The title compound, MS: m/e=299.2 (M+H$^+$), was prepared in accordance with the general method of example 1 from 3-(2-methyl-1H-imidazol-4-ylethynyl)-benzonitrile and 2-fluoro-4-methylpyridine.

EXAMPLE 7

2-Chloro-5-[4-(3-chloro-phenylethynyl)-2-methyl-imidazol-1-yl]-pyridine

The title compound, MS: m/e=328.1 (M$^+$), was prepared in accordance with the general method of example 1 from 4-(3-chloro-phenylethynyl)-2-methyl-1H-imidazole and 2-chloro-5-fluoro-pyridine.

EXAMPLE 8

5-[4-(3-Chloro-phenylethynyl)-2-methyl-imidazol-1-yl]-3-methyl-pyridazine

The title compound, MS: m/e=309.2 (M+H$^+$), was prepared in accordance with the general method of example 1 from 4-(3-chloro-phenylethynyl)-2-methyl-1H-imidazole and 5-chloro-3-methyl-pyridazine.

EXAMPLE 9

4-(3-Chloro-phenylethynyl)-1-furan-3-yl-2-methyl-1H-imidazole 4-(3-Chloro-phenylethynyl)-2-methyl-1H-imidazole (200 mg, 0.92 mmol) was dissolved in 10 mL dichloromethane. Powdered molecular sieves (3 A, 200 mg), 3-furaneboronic acid (207 mg, 1.85 mmol) and [Cu(OH)TMEDA]$_2$Cl$_2$ (43 mg, 0.093 mmol) were added. Oxygen was bubbled through the reaction mixture for 10 minutes and stirring was continued at room temperature overnight. The reaction mixture was filtered through a dicalite speed plus pad and washed with 50 mL dichloromethane. The filtrate was washed with 50 mL water, dried with magnesium sulfate, filtered and evaporated. The crude product was purified by flash chromatography on silica gel (dichloromethane/methanol 100:0->90:10 gradient) and the desired compound was as a brown oil (21 mg, 8%), MS: m/e=283.1 (M+H$^+$).

EXAMPLE 10

2-[4-(3-Chloro-phenylethynyl)-2-methyl-imidazol-1-yl]-4-methyl-pyrimidine

The title compound, MS: m/e=309.1 (M+H$^+$), was prepared in accordance with the general method of example 1 from 4-(3-chloro-phenylethynyl)-2-methyl-1H-imidazole and 2-chloro-4-methyl-pyrimidine (prepared according to Harden, D. B.; Makrosz, M. J.; Strekowski, L.; *J. Org. Chem.* 1988, 53, 4137).

EXAMPLE 11

2-[4-(3-Chloro-phenylethynyl)-2-methyl-imidazol-1-yl]-5-fluoro-pyrimidine

The title compound, MS: m/e=313.1 (M+H$^+$), was prepared in accordance with the general method of example 1 from 4-(3-chloro-phenylethynyl)-2-methyl-1H-imidazole and 2-chloro-5-fluoro-pyrimidine.

EXAMPLE 12

3-[4-(3-Chloro-phenylethynyl)-2-methyl-imidazol-1-yl]-6-methyl-pyridazine

The title compound, MS: m/e=309.3 (M+H$^+$), was prepared in accordance with the general method of example 1 from 4-(3-chloro-phenylethynyl)-2-methyl-1H-imidazole and 3-chloro-6-methyl-pyridazine.

EXAMPLE 13

2-[4-(3-Chloro-phenylethynyl)-2-methyl-imidazol-1-yl]-6-methyl-pyridine

The title compound, MS: m/e=308.2 (M+H$^+$), was prepared in accordance with the general method of example 1 from 4-(3-chloro-phenylethynyl)-2-methyl-1H-imidazole and 2-fluoro-6-methyl-pyridine.

EXAMPLE 14

2-[4-(3-Chloro-phenylethynyl)-2-methyl-imidazol-1-yl]-6-trifluoromethyl-pyridine The title compound, MS: m/e=362.2 (M+H$^+$), was prepared in accordance with the general method of example 1 from 4-(3-chloro-phenylethynyl)-2-methyl-1H-imidazole and 2-fluoro-6-trifluoromethyl-pyridine.

EXAMPLE 15

2-[4-(3-Chloro-phenylethynyl)-2-methyl-imidazol-1-yl]-5-methyl-pyridine

The title compound, MS: m/e=308.2 (M+H$^+$), was prepared in accordance with the general method of example 1 from 4-(3-chloro-phenylethynyl)-2-methyl-1H-imidazole and 2-fluoro-5-methyl-pyridine.

EXAMPLE 16

2-[4-(3-Chloro-phenylethynyl)-2-methyl-imidazol-1-yl]-4-methyl-pyridine

The title compound, MS: m/e=308.2 (M+H$^+$), was prepared in accordance with the general method of example 1 from 4-(3-chloro-phenylethynyl)-2-methyl-1H-imidazole and 2-fluoro-4-methyl-pyridine.

EXAMPLE 17

3-[4-(3-Chloro-phenylethynyl)-2-methyl-imidazol-1-yl]-5-fluoro-pyridine

The title compound, MS: m/e=312.1 (M+H$^+$), was prepared in accordance with the general method of example 1 from 4-(3-chloro-phenylethynyl)-2-methyl-1H-imidazole and 3,5-difluoro-pyridine.

EXAMPLE 18

2-[4-(3-Chloro-phenylethynyl)-2-methyl-imidazol-1-yl]-4-methyl-pyrimidine

The title compound, MS: m/e=309.1 (M+H$^+$), was prepared in accordance with the general method of example 1 from 4-(3-chloro-phenylethynyl)-2-methyl-1H-imidazole and 2-chloro-4-methyl-pyrimidine.

EXAMPLE 19

3-[2-Methyl-1-(4-methyl-pyrimidin-2-yl)-1H-imidazol-4-ylethynyl]-benzonitrile

The title compound, MS: m/e=300.4 (M+H$^+$), was prepared in accordance with the general method of example 1 from 3-(2-methyl-1H-imidazol-4-ylethynyl)-benzonitrile and 2-chloro-4-methyl-pyrimidine.

EXAMPLE 20

3-[1-(4-Methoxy-pyrimidin-2-yl)-2-methyl-1H-imidazol-4-ylethynyl]-benzonitrile

The title compound, MS: m/e=316.1 (M+H$^+$), was prepared in accordance with the general method of example 1 from 3-(2-methyl-1H-imidazol-4-ylethynyl)-benzonitrile and 2-chloro-4-methoxypyrimidine.

EXAMPLE 21

2-[4-(3-Chloro-phenylethynyl)-2-methyl-imidazol-1-yl]-pyrazine

The title compound, MS: m/e=295.3 (M+H$^+$), was prepared in accordance with the general method of example 1 from 4-(3-chloro-phenylethynyl)-2-methyl-1H-imidazole and 2-chloropyrazine.

EXAMPLE 22

3-(2-Methyl-1-pyrazin-2-yl-1H-imidazol-4-ylethynyl)-benzonitrile

The title compound, MS: m/e=286.1 (M+H$^+$), was prepared in accordance with the general method of example 1 from 3-(2-methyl-1H-imidazol-4-ylethynyl)-benzonitrile and 2-chloropyrazine.

EXAMPLE 23

4-[4-(3-Chloro-phenylethynyl)-2-methyl-imidazol-1-yl]-pyrimidine

The title compound, MS: m/e=294.1/296.1 (M+H$^+$), was prepared in accordance with the general method of example 1 from 4-(3-chloro-phenylethynyl)-2-methyl-1H-imidazole and 4-chloro-pyrimidine.

EXAMPLE 24

3-[4-(3-Chloro-phenylethynyl)-2-methyl-imidazol-1-yl]-6-methyl-pyridazine

The title compound, MS: m/e=309.3 (M+H$^+$), was prepared in accordance with the general method of example 1 from 4-(3-chloro-phenylethynyl)-2-methyl-1H-imidazole and 3-chloro-6-methylpyrazine.

EXAMPLE 25

3-Chloro-6-[4-(3-chloro-phenylethynyl)-2-methyl-imidazol-1-yl]-pyridazine

The title compound, MS: m/e=329.1 (M$^+$), was prepared in accordance with the general method of example 1 from 4-(3-chloro-phenylethynyl)-2-methyl-1H-imidazole and 3,6-dichloropyridazine.

EXAMPLE 26

3-[4-(3-Chloro-phenylethynyl)-2-methyl-imidazol-1-yl]-6-methoxy-pyridazine

3-Chloro-6-[4-(3-chloro-phenylethynyl)-2-methyl-imidazol-1-yl]-pyridazine (100 mg, 0.30 mmol) was dissolved in 2 mL methanol and 1.5 mL sodium methanolate solution were added. The reaction mixture was refluxed for 3 h. After cooling to room temperature the reaction mixture was treated with 30 mL water and extracted three times with ethyl acetate (50 mL each). The combined organic extracts were dried with magnesium sulfate, filtered and evaporated and the desired product was obtained as a white solid (53 mg, 53%), MS: m/e=325.3 (M+H⁺).

EXAMPLE 27

{6-[4-(3-Chloro-phenylethynyl)-2-methyl-imidazol-1-yl]-pyridazin-3-yl}-dimethyl-amine 3-Chloro-6-[4-(3-chloro-phenylethynyl)-2-methyl-imidazol-1-yl]-pyridazine (100 mg, 0.30 mmol) was dissolved in 2 mL dimethylforamide and dimethyl-amine hydrochloride (124 mg, 1.5 mmol) and cesium carbonate (396 mg, 1.2 mmol) were added. The reaction mixture was heated in the microwave at 140° C. for 60 min. After cooling to room temperature the reaction mixture was treated with 50 mL water and extracted three times with ethyl acetate (50 mL each). The combined organic extracts were dried with magnesium sulfate, filtered and evaporated. The crude material was purified by flash chromatography (methylene chloride/methanol 100:0->90:10 gradient) and the desired product was obtained as a white solid (57 mg, 55%), MS: m/e=338.1 (M+H⁺).

EXAMPLE 28

2-[4-(3-Chloro-phenylethynyl)-2-methyl-imidazol-1-yl]-6-methyl-pyridine

The title compound, MS: m/e=308.2 (M⁺), was prepared in accordance with the general method of example 1 from 4-(3-chloro-phenylethynyl)-2-methyl-1H-imidazole and 2-fluoro-6-methylpyridine.

EXAMPLE 29

2-[4-(3-Chloro-phenylethynyl)-2-methyl-imidazol-1-yl]-6-trifluoromethyl-pyridine The title compound, MS: m/e=362.2 (M⁺), was prepared in accordance with the general method of example 1 from 4-(3-chloro-phenylethynyl)-2-methyl-1H-imidazole and 2-fluoro-6-trifluoromethyl-pyridine.

EXAMPLE 30

2-[4-(3-Chloro-phenylethynyl)-2-methyl-imidazol-1-yl]-5-methyl-pyridine

The title compound, MS: m/e=308.2 (M⁺), was prepared in accordance with the general method of example 1 from 4-(3-chloro-phenylethynyl)-2-methyl-1H-imidazole and 2-fluoro-5-methylpyridine.

EXAMPLE 31

5-Methyl-2-[2-methyl-4-(3-trifluoromethyl-phenylethynyl)-imidazol-1-yl]-pyridine The title compound, MS: m/e=342.1 (M⁺), was prepared in accordance with the general method of example 1 from 2-methyl-4-(3-trifluoromethyl-phenylethynyl)-1H-imidazole and 2-fluoro-5-methylpyridine.

EXAMPLE 32

2-[4-(3-Chloro-phenylethynyl)-2-methyl-imidazol-1-yl]-4-methyl-pyridine

The title compound, MS: m/e=308.2 (M⁺), was prepared in accordance with the general method of example 1 from 4-(3-chloro-phenylethynyl)-2-methyl-1H-imidazole and 2-fluoro-4-methylpyridine.

EXAMPLE 33

2-Chloro-5-[2-methyl-4-(3-trifluoromethyl-phenylethynyl)-imidazol-1-yl]-pyridine The title compound, MS: m/e=362.3 (M⁺), was prepared in accordance with the general method of example 1 from 2-methyl-4-(3-trifluoromethyl-phenylethynyl)-1H-imidazole and 2-chloro-5-fluoro-pyridine.

EXAMPLE 34

3-[4-(3-Chloro-phenylethynyl)-2-methyl-imidazol-1-yl]-5-fluoro-pyridine

The title compound, MS: m/e=312.1 (M⁺), was prepared in accordance with the general method of example 1 from 4-(3-chloro-phenylethynyl)-2-methyl-1H-imidazole and 3,5-difluoro-pyridine.

EXAMPLE 35

3-[1-(5-Fluoro-pyridin-3-yl)-2-methyl-1H-imidazol-4-ylethynyl]-benzonitrile

The title compound, MS: m/e=303.5 (M⁺), was prepared in accordance with the general method of example 1 from 3-(2-methyl-1H-imidazol-4-ylethynyl)-benzonitrile and 3,5-difluoro-pyridine.

EXAMPLE 36

3-Fluoro-5-[2-methyl-4-(3-trifluoromethyl-phenylethynyl)-imidazol-1-yl]-pyridine The title compound, MS: m/e=346.3 (M⁺), was prepared in accordance with the general method of example 1 from 2-methyl-4-(3-trifluoromethyl-phenylethynyl)-1H-imidazole and 3,5-difluoro-pyridine.

EXAMPLE 37

{5-[4-(3-Chloro-phenylethynyl)-2-methyl-imidazol-1-yl]-pyridin-3-yl}-dimethyl-amine The title compound, MS: m/e=337.3 (M⁺), was prepared in accordance with the general method of example 27 from 3-[4-(3-chloro-phenylethynyl)-2-methyl-imidazol-1-yl]-5-fluoro-pyridine and dimethylamine hydrochloride.

EXAMPLE 38

3-[1-(5-Dimethylamino-pyridin-3-yl)-2-methyl-1H-imidazol-4-ylethynyl]-benzonitrile The title compound, MS: m/e=328.4 (M⁺), was prepared in accordance with the general method of example 27 from 3-[1-(5-fluoro-pyridin-3-yl)-2-methyl-1H-imidazol-4-yl-ethynyl]-benzonitrile and dimethylamine hydrochloride.

EXAMPLE 39

4-{6-[4-(3-Chloro-phenylethynyl)-2-methyl-imidazol-1-yl]-pyridin-2-yl}-thiomorpholine The title compound, MS: m/e=395.1, 397.1 (M+H⁺), was prepared in accordance with the general method of example 27 from 2-[4-(3-chloro-phenylethynyl)-2-methylimidazol-1-yl]-6-fluoro-pyridine and thiomorpholine.

EXAMPLE 40

4-{6-[4-(3-Chloro-phenylethynyl)-2-methyl-imidazol-1-yl]-pyridin-2-yl}-thiomorpholine-1,1-dioxide 4-{6-[4-(3-Chloro-phenylethynyl)-2-methyl-imidazol-1-yl]-pyridin-2-yl}-thiomorpholine (250 mg, 0.63 mmol) was dissolved in 6 mL of methanol and Oxone monopersulfate triple salt (389 mg, 0.63 mmol) was added. The reaction mixture was stirred at room temperature for 4 days. Then additional Oxone monopersulfate triple salt (78 mg, 1.3 mmol) was added to drive the reaction to completion. The reaction mixture was treated with 50 mL water. The pH was adjusted to 9 by addition of sat. sodium bicarbonate solution, and the reaction mixture was extracted three times with methylene chloride (50 mL each). The combined organic extracts were dried with magnesium sulfate, filtered and evaporated. The crude material was purified by flash chromatography (heptane/ethyl acetate 1:4) and the desired product was obtained as a white solid (97 mg, 36%), MS: m/e=427.4, 429.4 (M+H⁺).

Synthesis of Intermediates:

EXAMPLE A 4-(3-Chloro-phenylethynyl)-2-methyl-1H-imidazole

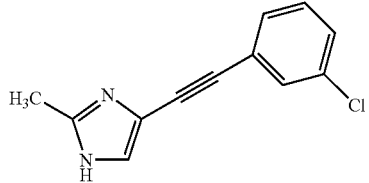

Step 1
(3-Chloro-phenylethynyl)-trimethyl-silane
Chloro-3-iodobenzene (10.0 g, 41.9 mmol) was dissolved in 100 mL dry THF and 17.5 mL triethyl amine. This mixture was evacuated and backfilled with argon several times to remove oxygen from the solution. Triphenylphosphine (329 mg, 1.25 mmol) and bis(triphenylphosphine)palladium(II)chloride (1.47 g, 2.09 mmol) were added and the reaction mixture was stirred at room temperature for 1 h. Copper(I)iodide (239 mg, 1.25 mmol) and trimethylsilylacetylen (6.28 g, 6.39 mmol) were added. The reaction mixture was stirred at room temperature overnight. The solvent was evaporated. The residue was taken up in 500 mL water and extracted three times with ethyl acetate (500 mL each). The combined organic extracts were dried with magnesium sulfate, filtered and evaporated. The crude product was purified by flash-chromatography on silica gel (heptane/ethyl acetate 100:0->80:20 gradient). The desired product was obtained as a light yellow oil (7.38 g, purity ~70%, yield ~59%).

Step 2
4-(3-Chloro-phenylethynyl)-2-methyl-1H-imidazole
Solution 1: (3-Chloro-phenylethynyl)-trimethyl-silane (7.1 g, 70%, 23.8 mmol) and 5-iodo-2-methyl-1H-imidazole (4.5 g, 21.6 mmol, synthesis: M. D. Cliff, S. G. Pyne, *Synthesis* 1994, 681–682) were dissolved in 50 mL dry THF and 5 mL dry DMF. This mixture was evacuated and backfilled with argon several times to remove oxygen from the solution.

Solution 2: Triphenylphosphine (113 mg, 0.43 mmol), bis(triphenylphosphine)palladium(II)chloride (910 mg, 1.30 mmol), copper(I)iodide (41 mg, 0.22 mmol) and triethyl amine (4.52 mL, 32 mmol) were dissolved in 50 mL dry THF. This mixture was also evacuated and backfilled with argon several times to remove oxygen from the solution Solution 2 was heated to 40° C. and solution 1 was added dropwise. The reaction mixture was heated to 60° C. and tetrabutylammonium fluoride solution (1 M in THF, 28 mL, 28 mmol) was added dropwise during 45 min. The reaction was than stirred at room temperature overnight. The solvent was evaporated. The residue was taken up in 200 mL water and extracted three times with ethyl acetate (200 mL each). The combined organic extracts were dried with magnesium sulfate, filtered and evaporated. The crude product was purified by flash-chromatography on silica gel (methylene chloride/methanol 100:0->95:5 gradient) and the desired product was obtained as a light brown solid (6.93 g, purity ~50%, yield ~74%). This material which still contained tetrabutylammonium salts was used without any further purification for the next step.

EXAMPLE B 3-(2-methyl-1H-imidazol-4-ylethynyl)-benzonitrile

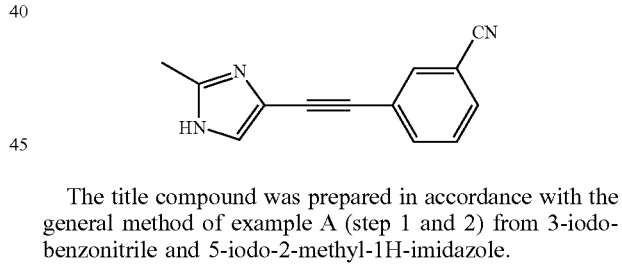

The title compound was prepared in accordance with the general method of example A (step 1 and 2) from 3-iodo-benzonitrile and 5-iodo-2-methyl-1H-imidazole.

EXAMPLE C

5-Chloro-3-methyl-pyridazine

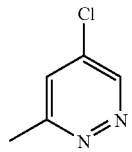

Step 1
3-Methyl-pyridazine-2-oxide
3-Methylpyridazine (10 g, 106 mmol) was dissolved in 62 mL acetic acid and hydrogen peroxide (30% in water, 58 mL, 568 mmol) was added. The reaction mixture was heated at reflux for 6 h and the solvents were evaporated. The residue was taken up in 200 mL water, neutralized with sodium carbonate and extracted three times with dichloromethane (150 mL each). The combined organic extracts were dried with magnesium sulfate, filtered and evaporated. The crude product was purified by three consecutive recrystallizations from toluene and the desired product was obtained as a white solid (800 mg, 6%).

Step 2

6-Methyl-4-nitro-pyridazine-1-oxide

3-Methyl-pyridazine-1-oxide (450 mg, 4.09 mmol) was dissolved in 2 mL conc. sulfuric acid. Nitric acid (0.47 mL, 11.4 mmol) was added dropwise and the reaction mixture was heated at reflux for 4 h. The reaction mixture was carefully poured into crushed ice and the mixture was extracted three times with dichloromethane (50 mL each). The combined organic extracts were dried with magnesium sulfate, filtered and evaporated. The crude product (270 mg, 42%) was used without any further purification for the next step.

Step 3

4-Bromo-6-methyl-pyridazine-1-oxide

6-Methyl-4-nitro-pyridazine-1-oxide (270 mg, 1.74 mmol) was dissolved in 2 mL acetic acid, acetyl bromide (650 mL, 8.7 mmol) was added and the reaction mixture was heated at reflux for 1 h. The reaction mixture was poured into crushed ice, the mixture was neutralized by addition of sodium hydroxide and extracted three times with dichloromethane (50 mL each). The combined organic extracts were dried with magnesium sulfate, filtered and evaporated. The crude product was purified by flash-chromatography on silica gel (heptane/ethyl acetate 80:20->30:70 gradient) and the desired product was obtained as a light brown solid (150 mg, 45%).

Step 4

5-Chloro-3-methyl-pyridazine

4-Bromo-6-methyl-pyridazine-1-oxide (150 mg, 0.79 mmol) was dissolved in 5 mL chloroform. Phosphorus trichloride (501 mg, 3.65 mmol, dissolved in 1 mL chloroform) was added at 0° C. The reaction mixture was stirred at room temperature for 36 h and then poured into crushed ice. The mixture was neutralized by addition of sodium carbonate and extracted three times with dichloromethane (50 mL each). The combined organic extracts were dried with magnesium sulfate, filtered and evaporated. The crude product was purified by flash-chromatography on silica gel (heptane/ethyl acetate 80:20->30:70 gradient) and the desired product was obtained as a brown oil (70 mg, 69%).

EXAMPLE D

5-Chloro-3-methyl-pyridazine

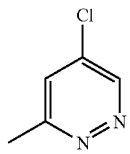

Step 1: 3-Methyl-pyridazine-1-oxide

3-Methylpyridazine (10 g, 106 mmol) was dissolved in 62 mL acetic acid and hydrogen peroxide (30% in water, 58 mL, 568 mmol) was added. The reaction mixture was heated at reflux for 6 h and the solvents were evaporated. The residue was taken up in 200 mL water, neutralized with sodium carbonate and extracted three times with dichloromethane (150 mL each). The combined organic extracts were dried with magnesium sulfate, filtered and evaporated. The crude product was purified by three consecutive recrystallizations from toluene and the desired product was obtained as a white solid (800 mg, 6%).

Step 2: 6-Methyl-4-nitro-pyridazine-1-oxide

3-Methyl-pyridazine-1-oxide (450 mg, 4.09 mmol) was dissolved in 2 mL conc. sulfuric acid. Nitric acid (0.47 mL, 11.4 mmol) was added dropwise and the reaction mixture was heated at reflux for 4 h. The reaction mixture was carefully poured into crushed ice and the mixture was extracted three times with dichloromethane (50 mL each). The combined organic extracts were dried with magnesium sulfate, filtered and evaporated. The crude product (270 mg, 42%) was used without any further purification for the next step.

Step 3: 4-Bromo-6-methyl-pyridazine-1-oxide

6-Methyl-4-nitro-pyridazine-1-oxide (270 mg, 1.74 mmol) was dissolved in 2 mL acetic acid, acetyl bromide (650 mL, 8.7 mmol) was added and the reaction mixture was heated at reflux for 1 h. The reaction mixture was poured into crushed ice, the mixture was neutralized by addition of sodium hydroxide and extracted three times with dichloromethane (50 mL each). The combined organic extracts were dried with magnesium sulfate, filtered and evaporated. The crude product was purified by flash-chromatography on silica gel (heptane/ethyl acetate 80:20->30:70 gradient) and the desired product was obtained as a light brown solid (150 mg, 45%).

Step 4: 5-Chloro-3-methyl-pyridazine

4-Bromo-6-methyl-pyridazine-1-oxide (150 mg, 0.79 mmol) was dissolved in 5 mL chloroform. Phosphorus trichloride (501 mg, 3.65 mmol, dissolved in 1 mL chloroform) was added at 0° C. The reaction mixture was stirred at room temperature for 36 h and then poured into crushed ice. The mixture was neutralized by addition of sodium carbonate and extracted three times with dichloromethane (50 mL each). The combined organic extracts were dried with magnesium sulfate, filtered and evaporated. The crude product was purified by flash-chromatography on silica gel (heptane/ethyl acetate 80:20->30:70 gradient) and the desired product was obtained as a brown oil (70 mg, 69%).

EXAMPLE E

2-[4-(3-Chloro-phenylethynyl)-2-methyl-imidazol-1-yl]-6-fluoro-pyridine

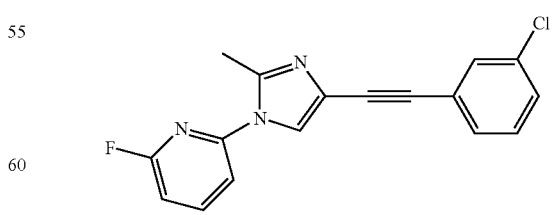

The title compound, MS: m/e=312.0, 314.0 (M+H$^+$), was prepared in accordance with the general method of example 1 from 4-(3-chloro-phenylethynyl)-2-methyl-1H-imidazole and 2,6-difluoro-pyridine.

Preparation of the pharmaceutical compositions:

EXAMPLE I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I

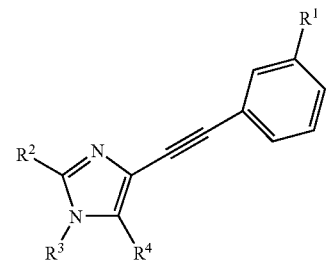

wherein
$R^1$ is selected from the group consisting of halogen, lower alkyl, lower alkoxy, $CF_3$, $CF_2H$, $OCF_3$, $OCF_2H$, and cyano;
$R^2$ is lower alkyl;
$R^3$ is selected from
  heteroaryl, and
  heteroaryl substituted by one, two or three substituents, selected from the group consisting of
    halogen,
    lower alkyl,
    cycloalkyl,
    lower alkyl-halogen,
    cyano,
    lower alkoxy,
    NR'R",
    1-morpholinyl,
    1-pyrrolidinyl,
    1-pyrrolidinyl substituted by —OR or $CH_2OR$,
    piperidinyl,
    piperidinyl substituted by —OR or $CH_2OR$,
    thiomorpholinyl,
    1-oxo-thiomorpholinyl,
    1,1-dioxo-thiomorpholinyl,
    piperazinyl, and
    piperazinyl substituted by a substituent selected from lower alkyl, cycloalkyl and $CH_2$-cycloalkyl;
R is selected from the group consisting of hydrogen, lower alkyl, cycloalkyl and $CH_2$-cycloalkyl;
R' and R" are each independently selected from the group consisting of hydrogen, lower alkyl, cycloalkyl, $CH_2$-cycloalkyl, —OR and $CH_2$—OR;
$R^4$ is selected from the group consisting of hydrogen, C(O)H, and $CH_2R^5$; and
$R^5$ is selected from the group consisting of hydrogen, OH, $C_1$–$C_6$-alkyl, and $C_3$–$C_{12}$-cycloalkyl;
or a pharmaceutically acceptable salt thereof.

2. A compound according to claim 1 of formula

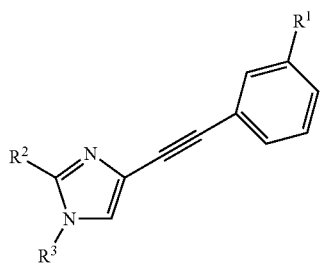

wherein
R¹ is selected from the group consisting of halogen, lower alkyl, lower alkoxy, CF₃ and cyano;
R² is lower alkyl;
R³ is selected from
  heteroaryl, and
  heteroaryl substituted by one, two or three substituents, selected from the group consisting of
    halogen,
    lower alkyl,
    lower alkyl-halogen,
    cyano,
    NR'R",
    1-morpholinyl,
    1-pyrrolidinyl,
    1-pyrrolidinyl substituted by —OR or CH₂OR,
    piperidinyl,
    piperidinyl substituted by —OR or CH₂OR,
    1,1-dioxo-thiomorpholinyl,
    piperazinyl, and
    piperazinyl substituted by a substituent selected from the group consisting of lower alkyl, cycloalkyl and CH₂-cycloalkyl;
R is selected from the group consisting of hydrogen, lower alkyl, cycloalkyl or CH₂-cycloalkyl; and
R' and R" are independently selected from the group consisting of hydrogen, lower alkyl, cycloalkyl, CH₂-cycloalkyl, OR and CH₂OR;
or a pharmaceutically acceptable salt thereof.

3. The compound of formula I in accordance with claim 1, wherein R¹ is chloro or cyano.

4. The compound of formula I in accordance with claim 3, wherein R³ is unsubstituted or substituted pyrimidin-2yl.

5. The compound of formula I in accordance with claim 4, wherein the compound is selected from
2-[4-(3-chloro-phenylethynyl)-2-methyl-imidazol-1-yl]-pyrimidine,
2-[4-(3-chloro-phenylethynyl)-2-methyl-imidazol-1-yl]-4-trifluoromethyl-pyrimidine,
2-[4-(3-chloro-phenylethynyl)-2-methyl-imidazol-1-yl]-4-methyl-pyrimidine,
2-[4-(3-chloro-phenylethynyl)-2-methyl-imidazol-1-yl]-5-fluoro-pyrimidine and
3-[1-(4-methoxy-pyrimidin-2-yl)-2-methyl-1H-imidazol-4-ylethynyl]-benzonitrile.

6. The compound of formula I in accordance with claim 3, wherein R³ is unsubstituted or substituted pyridin-2-yl.

7. The compound of formula I in accordance with claim 6, wherein the compound is selected from
3-[2-methyl-1-(6-methyl-pyridin-2-yl)-1H-imidazol-4-ylethynyl]-benzonitrile,
3-[2-methyl-1-(6-trifluoromethyl-pyridin-2-yl)-1H-imidazol-4-ylethynyl]-benzonitrile,
3-[2-methyl-1-(5-methyl-pyridin-2-yl)-1H-imidazol-4-ylethynyl]-benzonitrile,
3-[2-methyl-1-(4-methyl-pyridin-2-yl)-1H-imidazol-4-ylethynyl]-benzonitrile,
2-[4-(3-chloro-phenylethynyl)-2-methyl-imidazol-1-yl]-6-methyl-pyridine and
2-[4-(3-chloro-phenylethynyl)-2-methyl-imidazol-1-yl]-6-trifluoromethyl-pyridine.

8. The compound of formula I in accordance with claim 6, wherein the compound is selected from
2-[4-(3-chloro-phenylethynyl)-2-methyl-imidazol-1-yl]-5-methyl-pyridine,
3-[4-(3-chloro-phenylethynyl)-2-methyl-imidazol-1-yl]-5-fluoro-pyridine,
2-[4-(3-chloro-phenylethynyl)-2-methyl-imidazol-1-yl]-5-methyl-pyridine,
2-[4-(3-chloro-phenylethynyl)-2-methyl-imidazol-1-yl]-4-methyl-pyridine,
3-[4-(3-chloro-phenylethynyl)-2-methyl-imidazol-1-yl]-5-fluoro-pyridine and
4-{6-[4-(3-chloro-phenylethynyl)-2-methyl-imidazol-1-yl]-pyridin-2-yl}-thiomorpholine.

9. The compound of formula I in accordance with claim 3, wherein R³ is unsubstituted or substituted pyridin-3-yl.

10. The compound of formula I in accordance with claim 9, wherein the compound is selected from
2-chloro-5-[4-(3-chloro-phenylethynyl)-2-methyl-imidazol-1-yl]-pyridine and
2-[4-(3-chloro-phenylethynyl)-2-methyl-imidazol-1-yl]-4-methyl-pyridine.

11. The compound of formula I in accordance with claim 3, wherein R³ is selected from pyridazinyl, substituted pyridazinyl, pyrazinyl and substituted pyrazinyl.

12. The compound of formula I in accordance with claim 11, wherein the compound is selected from
5-[4-(3-chloro-phenylethynyl)-2-methyl-imidazol-1-yl]-3-methyl-pyridazine,
3-[4-(3-chloro-phenylethynyl)-2-methyl-imidazol-1-yl]-6-methyl-pyridazine and
2-[4-(3-chloro-phenylethynyl)-2-methyl-imidazol-1-yl]-pyrazine.

13. The compound of formula I in accordance with claim 3, wherein R³ is furan-3-yl.

14. The compound of formula I in accordance with claim 13, wherein the compound is 5-(3-chloro-phenylethynyl)-1-furan-3-yl-2-methyl-1H-imidazole.

15. A pharmaceutical composition which comprises a compound of formula I

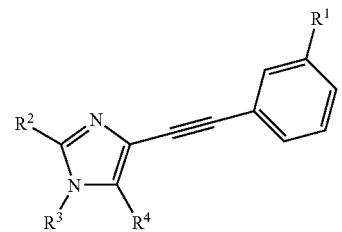

wherein,
R¹ is selected from the group consisting of halogen, lower alkyl, lower alkoxy, CF₃, CF₂H, OCF₃, OCF₂H, and cyano;
R² is lower alkyl;
R³ is selected from
  heteroaryl,
  heteroaryl substituted by one, two or three substituents, selected from the
  group consisting of
    halogen,
    lower alkyl,
    cycloalkyl,
    lower alkyl-halogen,
    cyano,
    lower alkoxy,
    NR'R",
    1-morpholinyl,
    1-pyrrolidinyl,
    1-pyrrolidinyl substituted by —OR or CH₂OR, piperidinyl,
piperidinyl substituted by —OR or CH$_2$OR,
thiomorpholinyl,
1-oxo-thiomorpholinyl,
1,1-dioxo-thiomorpholinyl,
piperazinyl, and
piperazinyl substituted by a substituent selected from lower
alkyl, cycloalkyl and CH$_2$-cycloalkyl;
R is selected from the group consisting of hydrogen, lower alkyl, cycloalkyl and CH$_2$-cycloalkyl;
R' and R" are each independently selected from the group consisting of hydrogen, lower alkyl, cycloalkyl, CH$_2$-cycloalkyl, —OR and CH$_2$—OR;
R$^4$ is selected from hydrogen, C(O)H, and CH$_2$R$^5$;
R$^5$ is selected from the group consisting of hydrogen, OH, C$_1$–C$_6$-alkyl, and C$_3$–C$_{12}$-cycloalkyl;
or a pharmaceutically acceptable salt thereof;
and a pharmaceutically acceptable carrier.

* * * * *